US012611331B2

(12) United States Patent
Zhang et al.

(10) Patent No.: US 12,611,331 B2
(45) Date of Patent: Apr. 28, 2026

(54) METHOD FOR TREATING ADVANCED PRIMARY ANGLE CLOSURE GLAUCOMA

(71) Applicant: Zhongshan Ophthalmic Center of Sun Yat-sen University, Guangdong (CN)

(72) Inventors: Xiulan Zhang, Guangdong (CN); Fengbin Lin, Guangdong (CN); Yunhe Song, Guangdong (CN); Xinbo Gao, Guangdong (CN); Shida Chen, Guangdong (CN)

(73) Assignee: Zhongshan Ophthalmic Center of Sun Yat-sen University, Guangzhou (CN)

( * ) Notice: Subject to any disclaimer, the term of this patent is extended or adjusted under 35 U.S.C. 154(b) by 870 days.

(21) Appl. No.: 17/544,180

(22) Filed: Dec. 7, 2021

(65) Prior Publication Data

US 2023/0172752 A1 Jun. 8, 2023

(51) Int. Cl.
| | |
|---|---|
| *A61F 9/007* | (2006.01) |
| *A61F 9/00* | (2006.01) |
| *G02B 21/00* | (2006.01) |

(52) U.S. Cl.
CPC ........ *A61F 9/00781* (2013.01); *A61F 9/0008* (2013.01); *A61F 9/00754* (2013.01); *G02B 21/0012* (2013.01)

(58) Field of Classification Search
CPC .................................................. A61F 9/00781
See application file for complete search history.

(56) References Cited

U.S. PATENT DOCUMENTS

2020/0330266 A1* 10/2020 Junger .................... A61F 9/009

OTHER PUBLICATIONS

Dorairaj, S., Tam, M. D., & Balasubramani, G. K. (2019). Twelve-month outcomes of excisional goniotomy using the Kahook Dual BladeÂ® in eyes with angle-closure glaucoma. Clinical Ophthalmology, 13, 1779â1785. https://doi.org/10.2147/OPTH.S221299 (Year: 2019).*
Albert & Jakobiec's Principles & Practice of Ophthalmology, 3rd Edition Chapter 219—Laser and Surgery Treatment of Angle-Closure Glaucoma M. Roy Wilson, Mark Gallardo (Year: 2017).*
Finger, P.T. Small incision surgical iridotomy and iridectomy. Graefe's Arch Clin Exp Ophthalmo 244, 399â400 (2006). https://doi.org/10.1007/s00417-005-0071-y (Year: 2005).*
Narsani, Ashok Kumar, Partab Rai Nagdev, and Maria Nazish Memon. "Outcome of recurrent pterygium with intraoperative 0.02% mitomycin C and free flap limbal conjunctival autograft." J Coll Physicians Surg Pak 23.3 (2013): 199-202. (Year: 2013).*

(Continued)

*Primary Examiner* — Erin McGrath
(74) *Attorney, Agent, or Firm* — MUNCY, GEISSLER, OLDS & LOWE, P.C.

(57) ABSTRACT

A method for treating advanced primary angle closure glaucoma (PACG) includes steps of: S1, utilizing surgical peripheral iridectomy (SPI) to eliminate pupillary block; S2, utilizing goinosynchialysis (GSL) to separate peripheral anterior synechia (PAS) in the anterior chamber angle with the assistance of a gonioscope and a chopper; and S3, utilizing goniotomy (GT) to incise a dysfunctional trabecular meshwork and a Schlemm canal, so as to remove a dysfunctional trabecular meshwork, enhance outflow of aqueous humor, and reduce intraocular pressure.

5 Claims, 2 Drawing Sheets

Left eye          Right eye

(56) References Cited

OTHER PUBLICATIONS

Tian, T., Li, M., Pan, Y. et al. The effect of phacoemulsification plus goniosynechialysis in acute and chronic angle closure patients with extensive goniosynechiae. BMC Ophthalmol 19, 65 (2019). https://doi.org/10.1186/s12886-019-1070-9 (Year: 2019).*

Monteiro de Barros, et al. The Early Flat Anterior Chamber After Trabeculectomy: A Randomized, Prospective Study of 3 Methods of Management. Journal of Glaucoma 18(1):p. 13-20, Jan. 2009. | DOI: 10.1097/IJG.0b013e31816f7647 (Year: 2009).*

Greenwood et al. Goniotomy with a single-use dual blade. J Cataract Refract Surg. Sep. 2017;43(9):1197-1201. doi: 10.1016/j.jcrs.2017.06.046. PMID: 28991617. (Year: 2017).*

* cited by examiner

METHOD FOR TREATING ADVANCED PRIMARY ANGLE CLOSURE GLAUCOMA

TECHNICAL FIELD

The present invention relates to the technical field of ophthalmic surgery, and in particular to a method for treating advanced primary angle closure glaucoma.

BACKGROUND ART

So far, trabeculectomy alone or combined with cataract phacoemulsification and intraocular lens implantation (PEI) are conventional interventions for treating advanced primary angle closure glaucoma (PACG). Trabeculectomy builds an artificial channel for outflow of intraocular aqueous humor from inside to outside, which may occur inevitable complications, such as, surgical failure caused by scarring of the filtration bleb, persistent low intraocular pressure or malignant glaucoma. Moreover, there is a long learning curve for trabeculectomy, and post-operation care of the filtration blebs is time-consuming and strenuous, so it is not an ideal surgery.

Researches at home and abroad in recent years have reported the superiority and safety of PEI for treating PACG. The popularization of the minimally invasive glaucoma surgery (MIGS) concept promotes the PEI-based MIGS surgery to become a new choice for treating the PACG. However, for patients with clear lens or no indications for PEI, is there an alternative of trabeculectomy?

Azuara-Blanco A et al. has shown that PACG patients with transparent lens extraction have more desirable intraocular pressure control and quality of life score than traditional drugs or laser peripheral iridectomy (LPI). However, in clinical practice, applying PEI in patients without indications of cataract surgery is still controversial, because early PEI will make the patient lose ocular accommodation, and be exposed to excessive light stimuli. Creatively incorporating MIGS in such patients in spare of transparent lens or conjunctiva has not been found in the database Pubmed yet, and the present invention now provides a method which will be illustrated below.

SUMMARY

With safe profile and minimally invasive injury, the present invention provides a method for treating advanced PACG, avoiding the complications of conventional filtration surgery.

According to the present invention, the method for treating advanced PACG includes:

S1, utilizing surgical peripheral iridectomy (SPI) to eliminate pupillary block;

S2, utilizing goinosynchialysis (GSL) to separate peripheral anterior synechia (PAS) in the anterior chamber angle with the assistance of a gonioscope and a chopper; and S3, utilizing goniotomy (GT) to incise trabecular meshwork and open Schlemm canal, so as to remove a dysfunctional trabecular meshwork, enhance outflow of aqueous humor, and reduce intraocular pressure.

The present invention aims to create a new method by changing conventional surgical ideas with incorporating MIGS and common technologies into the practice. The step of S1 solves the problem of pupillary block, a common etiology of PACG, by means of the SPI. The step of S2 solves the problem of insufficient and inaccurate separation of the anterior chamber angle adhesion by creatively applying the chopper in GSL under the gonioscope, and further solves the problems of operating difficulty arising from shallow anterior chamber by injecting a viscoelastic substance into the anterior chamber to increase operation space. The step of S3 solves the problem of remnant resistance of aqueous outflow by means of the GT, which removes the dysfunctional trabecular meshwork and facilitate the aqueous humor directly flowing into Schlemm canal and beyond, thereby finally achieving intraocular pressure reduction.

According to the present invention, the step of S1 can specifically include steps of:

S11, carrying out surface anesthesia on a surgical eye, and using 1%-2% pilocarpine for miosis;

S12, disinfecting a surgical drape after anesthesia, and utilizing an eye speculum to open eyelids;

S13, making a conjunctival incision with a length of about 2 mm superior-nasally along the corneal limbus, utilizing a hemostat for hemostasis, and then making a full-thickness corneal incision;

S14, pressing a posterior lip of the cornea incision to make the herniate of the peripheral iris tissue from cornea incision;

S15, utilizing microscopic smooth forceps to clamp the iris tissue, and then utilizing corneal scissors to cut off full-thickness iris tissue with an area of about 1.5 mm*1.5 mm.

In step of S12, a 6-0 silk suture on peripheral transparent cornea is optionally utilized for fixing the eyeball after the eyelids are opened by the eye speculum.

According to the present invention, the step of S2 may specifically include steps of:

S21, selecting a side of temporal quadrant or superior-temporal to make a transparent corneal incision with a length of about 2.2 mm as a main incision;

S22, injecting a viscoelastic substance into the anterior chamber;

S23, adjusting a head position of a patient and an inclination angle of a surgical microscope to directly view the anterior chamber angle structure under the gonioscope; and S24, with the assistance of the gonioscope, a chopper entering contralateral anterior chamber angle from the main incision and slightly pressing the root of an iris, so as to separate the adhesive anterior chamber angle by 120° until a lower ⅔ functional trabecular meshwork and a scleral spur are seen.

In the step of S2, the chopper has the advantages of lightness, and a wide bottom allowing contact with the adhesive peripheral iris in a larger range, which facilitates to easily open the anterior chamber angle.

The goniotomy (GT) is performed using microhook or microblade to incise the dysfunctional trabecular meshwork and the inner wall of Schlemm canal with a range of 120 degrees. Viscoelastic substance is injected to deepen the anterior chamber in surgery, so as to acquire the operation space, thereby solving the problems of the shallow anterior chamber and the operating difficulty.

According to the present invention, the step of S3 may specifically include:

S31, inserting microhook or microblade into the trabecular meshwork and entering the Schlemm canal to incise dysfunctional trabecular meshwork and inner wall of the Schlernm canal by 120°;

S32, carrying out suction to remove a viscoelastic substance and possible hyphema in an anterior chamber by irrigation and aspiration;

S33, forming an anterior chamber using a balanced salt solution;

S34, using tobramycin and dexamethasone ophthalmic ointment, 1% pilocarpine ophthalmic ointment and an eye pad to bind the surgical eye.

Compared with the prior art, the present invention has the beneficial effects:

The present invention aims to create a new method by changing conventional surgical ideas with incorporating minimal invasive procedures and common technologies, which is able to achieve minimally invasive surgical innovation of treatment for patients with PACG and no cataract surgery indication. The present invention can solve the problems of the pupillary block, a common etiology of PACG, by means of the SPI, and the operating difficulty operating difficulty arising from the shallow anterior chamber, and solve the problem of the insufficient and inaccurate PAS separation, and solve the problems of the dysfunction of the anterior chamber angle of the PACG and the incapacity to effectively filter the aqueous humor.

The surgery of the present invention is simple and effective, and may also effectively avoid complications of external filtration surgery.

What's more, learning curve of the surgery according to the present invention is short, which is easier to popularize in glaucoma doctors.

DETAILED DESCRIPTION

The accompanying drawings of the present invention are merely used for exemplary illustration, instead of being construed as limiting the present invention.

According to an embodiment, a method for treating advanced primary angle closure glaucoma (PACG) includes steps of:

S1, utilize surgical peripheral iridectomy (SPI) to eliminate pupillary block. The step of S1 specifically includes:

S11, carrying out surface anesthesia on a surgical eye, and using 1%-2% pilocarpine for miosis;

S12, disinfecting a surgical drape after anesthesia, and utilizing an eye speculum to open eyelids;

S13, making a conjunctival incision with a length of about 2 mm superior-nasally along a corneal limbus, utilizing a hemostat for hemostasis, and then making a full-thickness corneal incision;

S14, pressing a posterior lip of the cornea incision to make the herniate of the peripheral iris tissue from cornea incision;

S15, utilizing microscopic smooth forceps to clamp the iris tissue, and then utilizing corneal scissors to cut off full-thickness iris tissue with an area of about 1.5 mm*1.5 mm.

S2, utilize goinosynchialysis (GSL) to separate peripheral anterior synechia (PAS) with the assistance of a gonioscope and a chopper. The step of S2 specifically includes:

S21, selecting a side of temporal quadrant or superior-temporal to make a transparent corneal incision with a length of about 2.2 mm as a main incision;

S22, injecting the viscoelastic substance into the anterior chamber;

S23, adjusting a head position of a patient and an inclination angle of a surgical microscope so as to directly view an anterior chamber angle structure under the gonioscope; and S24, with the assistance of the gonioscope, a chopper entering contralateral anterior chamber angle from the main incision and slightly pressing the root of an iris, so as to separate the adhesive anterior chamber angle by 120° until a lower ⅔ functional trabecular meshwork and a scleral spur are seen.

S3, utilize Goniotomy (GT) to incise dysfunctional trabecular meshwork and open Schlemm canal. The step of S3 specifically includes:

S31, inserting microhook or microblade into the trabecular meshwork and entering the Schlemm canal to incise dysfunctional trabecular meshwork and inner wall of the Schlemm canal by 120°;

S32, carrying out suction to remove a viscoelastic substance and possible hyphema in an anterior chamber by irrigation and aspiration;

S33, forming an anterior chamber using a balanced salt solution;

S34, using tobramycin and dexamethasone ophthalmic ointment, 1% pilocarpine ophthalmic ointment and an eye pad to bind the surgical eye.

Separation and incision of the anterior chamber angle are mainly selected nasal or inferior-nasal quadrants of the angle, which are based on that more abundant distribution of a collecting tube system here, thereby effectively guaranteeing filtration efficiency of the aqueous humor, and fully reducing intraocular pressure.

Figure 1:
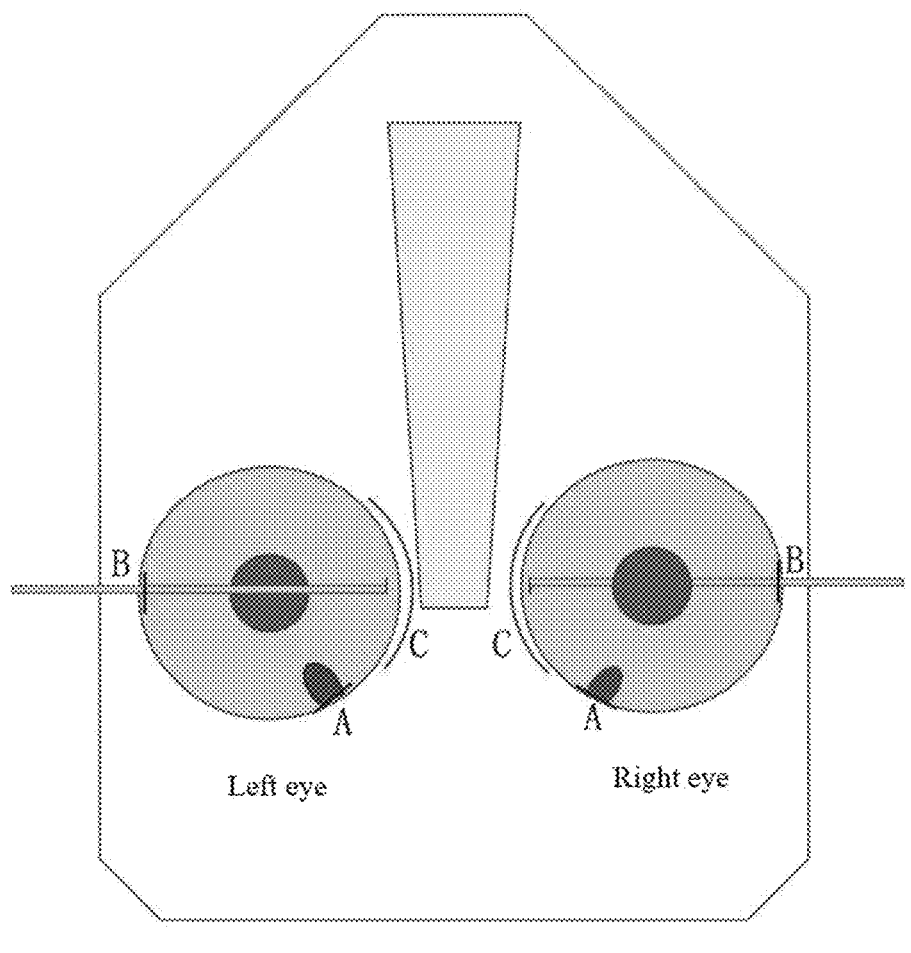
FIG. 1 is a positional schematic diagram I of carrying out SPI, GSL and GT of the present invention.

Specifically, as shown in FIG. 1, superior-nasal quadrant of the corneal limbus may be selected to carry out the SPI, where an oval shadow at a position A indicates a SPI; the incision is made on the side of the temporal quadrant to carry out the goinosynchialysis and the goniotomy, where a short line at a position B indicates the corneal incision; and the incision microhook or microblade enters anterior chamber, and the goniotomy is carried out within a 120° range at the nasal quadrant of the angle, where an arc at a position C indicates an incision range.

Figure 2:
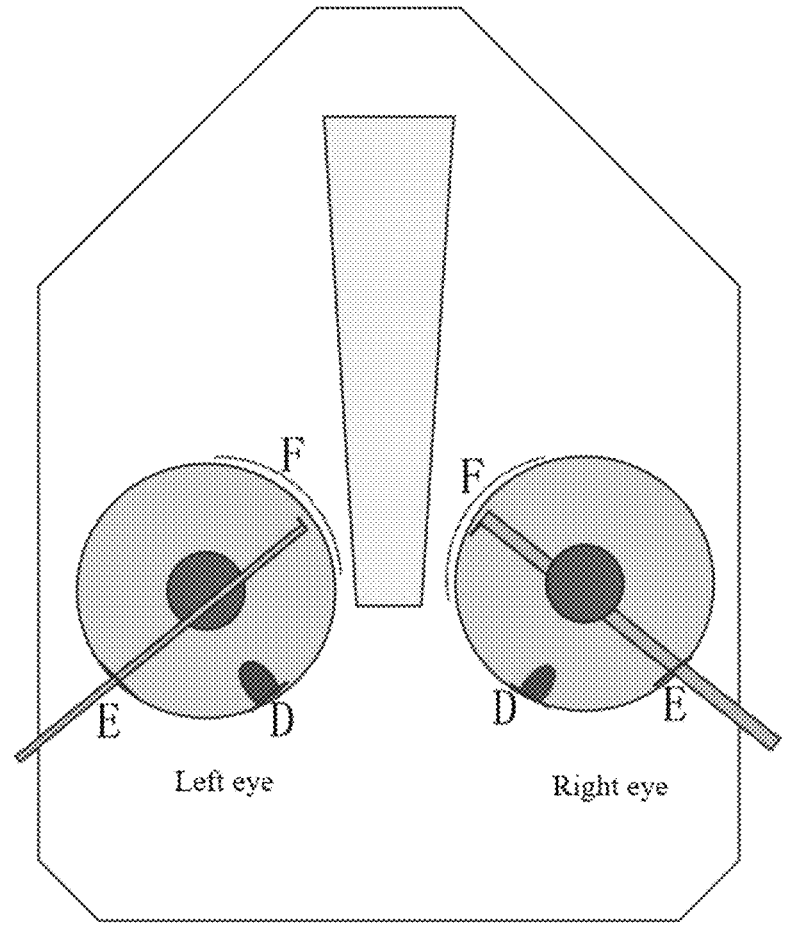
FIG. 2 is a positional schematic diagram II of carrying out the SPI, GSL and GT of the present invention.

As shown in FIG. 2, the head position of the patient further may be selected for operation, and the SPI is carried out at superior-nasal quadrant of the corneal limbus, where an oval shade at a position D indicates a SPI; the incision is made superior-temporally to carry out the goinosynchialysis and the goniotomy, where a short line at a position E indicates the incision; and the goniotomy is carried out within a 120° range inferior-nasally, where an arc at a position F indicates an incision range.

A difference between two surgical site selections in FIGS. 1 and 2 is that an operator is required to change a sitting position in surgery in FIG. 1, while the operator is not required to change a sitting position in surgery in FIG. 2.

Obviously, the above embodiment of the present invention is merely an example given for clearly illustrating the technical solution of the present invention, and is not intended to limit the specific embodiment of the present invention. Any modifications, equivalent replacements, improvements, etc. made within the spirit and principle of claims of the present invention shall should all fall within the scope of protection of claims of the present invention.

The invention claimed is:

1. A method for treating advanced primary angle closure glaucoma (PACG), comprising steps of:

S1, utilizing surgical peripheral iridectomy at a superior-nasal quadrant of a corneal limbus to eliminate pupillary block;

after utilizing the surgical peripheral iridectomy of S1, S2, utilizing goniosynechialysis to deepen an anterior chamber by injecting a viscoelastic substance into the anterior chamber and separate an anterior chamber angle, with the assistance of a gonioscope and a chopper with a wide bottom, so as to relieve physical adhesion of the anterior chamber angle; and after utilizing the goniosynechialysis of S2, S3, utilizing goniotomy to incise trabecular meshwork and open a Schlemm canal and to remove the injected viscoelastic substance in the anterior chamber, so as to remove a dysfunctional trabecular meshwork, enhance an outflow of aqueous humor, and reduce an intraocular pressure;

wherein S3 comprises:

S31, inserting a microhook or microblade into the trabecular meshwork and entering the Schlemm canal in the anterior chamber filled with the viscoelastic substance in the goniosynechialysis of S2 to incise the dysfunctional trabecular meshwork and an inner wall of the Schlemm canal by 120°;

S32, carrying out a suction to remove the viscoelastic substance and a possible hyphema in the anterior chamber by irrigation and aspiration after the S31 of incising the trabecular meshwork and the inner wall of the Schlemm canal;

S33, forming an anterior chamber using a balanced salt solution;

S34, using a tobramycin and dexamethasone ophthalmic ointment, a 1% pilocarpine ophthalmic ointment and an eye pad to bind the surgical eye.

2. The method according to claim 1, wherein S1 comprises:

S11, carrying out a surface anesthesia on a surgical eye, and using 1%-2% pilocarpine for miosis;

S12, disinfecting a surgical drape after the surface anesthesia, and utilizing an eye speculum to open eyelids;

S13, making a conjunctival incision with a length of 2 mm superior-nasally along the corneal limbus, utilizing a hemostat for hemostasis, and then making a full-thickness corneal incision;

S14, pressing a posterior lip of the cornea incision to make the herniate of the peripheral iris tissue from the cornea incision;

S15, utilizing microscopic smooth forceps to clamp the iris tissue, and then utilizing corneal scissors to cut off full-thickness iris tissue with an area of 1.5 mm*1.5 mm.

3. The method according to claim 2, wherein in step of S12, a 6-0 silk suture on a peripheral transparent cornea is optionally utilized for fixing the eyeball after the eyelids are opened by the eye speculum.

4. The method according to claim 1, wherein step S2 comprises the steps of:

S21, selecting a side of a temporal quadrant or a superior-temporal to make a transparent corneal incision with a length of 2.2 mm as a main incision;

S22, injecting the viscoelastic substance into the anterior chamber;

S23, adjusting a head position of a patient and an inclination angle of a surgical microscope to directly view the anterior chamber angle structure under the gonioscope; and S24, with the assistance of the gonioscope, the chopper entering contralaterally the anterior chamber angle from the main incision and slightly pressing a root of an iris, so as to separate the adhesive anterior chamber angle by 120° until a lower ⅔ functional trabecular meshwork and a scleral spur are seen.

5. The method according to claim 4, wherein in the step of S22, a head position of a patient and an inclination angle of a surgical microscope are adjusted to clearly and directly view an anterior chamber angle structure under the gonioscope.

* * * * *